US011518604B2

(12) United States Patent
Ou et al.

(10) Patent No.: US 11,518,604 B2
(45) Date of Patent: *Dec. 6, 2022

(54) SYSTEMS, METHODS AND DEVICES FOR AEROSOL SPRAYING OF SILICONE BASED TOPICAL SKIN ADHESIVES FOR SEALING WOUNDS

(71) Applicant: Ethicon, Inc., Somerville, NJ (US)

(72) Inventors: Duan Li Ou, Watchung, NJ (US); Carolyn J. Mordas, New Hope, PA (US)

(73) Assignee: Ethicon, Inc., Raritan, NJ (US)

( * ) Notice: Subject to any disclaimer, the term of this patent is extended or adjusted under 35 U.S.C. 154(b) by 97 days.

This patent is subject to a terminal disclaimer.

(21) Appl. No.: 16/885,426

(22) Filed: May 28, 2020

(65) Prior Publication Data

US 2021/0371190 A1   Dec. 2, 2021

(51) Int. Cl.
*B65D 83/30* (2006.01)
*A61L 26/00* (2006.01)
(Continued)

(52) U.S. Cl.
CPC .......... *B65D 83/30* (2013.01); *A61L 26/0019* (2013.01); *B65D 83/32* (2013.01);
(Continued)

(58) Field of Classification Search
CPC ........ B65D 83/30; B65D 83/32; B65D 83/66; A61L 26/0019; A61L 26/0076; C08L 83/04
(Continued)

(56) References Cited

U.S. PATENT DOCUMENTS 2,941,696 A * 6/1960 Homm ................... B65D 83/68
222/136
3,187,752 A   6/1965 Glick
(Continued)

FOREIGN PATENT DOCUMENTS

CN       104531056 A    4/2015
CN       105586001 A    5/2016
(Continued)

OTHER PUBLICATIONS

Lewis et al., "The chemistry of fumarate and maleate inhibitors with platinum hydrosilylation catalysts," Journal of Organometallic Chemistry, Aug. 23, 1996, pp. 221-227, vol. 521, No. 1, Elsevier, Amsterdam, NL.

(Continued)

*Primary Examiner* — Paul R Durand
*Assistant Examiner* — Michael J. Melaragno (57) ABSTRACT

An aerosol spray device includes a container having first and second fluid reservoirs disposed therein that are divided from one another. The first fluid reservoir holds a first mixture including a first aerosol propellant and a first part of a silicone based topical skin adhesive that is dissolved in the first aerosol propellant. The second fluid reservoir holds a second mixture including a second aerosol propellant and a second part of the silicone based topical skin adhesive that is dissolved in the second aerosol propellant. An aerosol spray dispensing system is connected with the container, which is configured to combine the first and second mixtures to form the silicone based topical skin adhesive and dispense the silicone based topical skin adhesive from the container as an aerosol spray.

20 Claims, 4 Drawing Sheets

(51) Int. Cl.
*B65D 83/32* (2006.01)
*B65D 83/66* (2006.01)
*C08L 83/04* (2006.01)

(52) U.S. Cl.
CPC .......... *B65D 83/66* (2013.01); *A61L 26/0076* (2013.01); *C08L 83/04* (2013.01)

(58) Field of Classification Search
USPC .................. 222/136, 145.1, 389; 424/43
See application file for complete search history.

(56) References Cited

U.S. PATENT DOCUMENTS

| | | | |
|---|---|---|---|
| 3,445,420 A | 5/1969 | Kookootsedes et al. | |
| 3,490,651 A * | 1/1970 | Abplanalp | B65D 83/14 222/94 |
| 3,675,821 A * | 7/1972 | Morane | B65D 83/64 222/80 |
| 3,775,452 A | 11/1973 | Karstedt | |
| 3,814,730 A | 6/1974 | Karstedt | |
| 4,234,108 A * | 11/1980 | Diamond | B65D 83/64 222/386 |
| 4,340,155 A * | 7/1982 | Obrist | B65D 83/42 222/135 |
| 4,791,149 A | 12/1988 | Pocknell | |
| 5,020,694 A * | 6/1991 | Pettengill | B65D 81/325 222/137 |
| 5,026,768 A | 6/1991 | Liles | |
| 5,211,316 A * | 5/1993 | Adalberto | B65D 83/62 222/386.5 |
| 5,431,303 A * | 7/1995 | Miskell | B65D 83/682 222/145.1 |
| 5,447,987 A | 9/1995 | Sato et al. | |
| 5,577,637 A * | 11/1996 | Voss | B05C 17/0052 137/625.18 |
| 5,647,510 A * | 7/1997 | Keller | B65D 81/3233 222/94 |
| 5,776,268 A | 7/1998 | Mcjames et al. | |
| 5,780,543 A | 7/1998 | Adachi et al. | |
| 6,265,480 B1 | 7/2001 | Enami et al. | |
| 6,537,246 B1 | 3/2003 | Unger et al. | |
| 6,613,185 B1 * | 9/2003 | Valade | C08L 83/04 156/329 |
| 6,951,654 B2 | 10/2005 | Malcolm et al. | |
| 7,393,547 B2 | 7/2008 | Nelson | |
| 7,481,333 B2 * | 1/2009 | Goldberg | B05C 17/0146 222/135 |
| 7,798,366 B2 * | 9/2010 | Hoshino | B65D 83/682 222/136 |
| 8,021,650 B2 * | 9/2011 | Tamareselvy | A61K 8/897 424/70.12 |
| 8,357,147 B2 | 1/2013 | Burkinshaw et al. | |
| 8,596,499 B2 * | 12/2013 | Vogt | B05C 11/1031 222/137 |
| 8,728,599 B2 | 5/2014 | Fang et al. | |
| 8,969,910 B2 | 3/2015 | Katayama | |
| 9,038,858 B2 * | 5/2015 | Hanai | B65D 83/62 222/135 |
| 9,180,476 B2 * | 11/2015 | Werner | B05B 11/3083 |
| 9,302,282 B2 * | 4/2016 | Bertin | B05B 7/2486 |
| 9,408,971 B2 | 8/2016 | Carlyon | |
| 9,422,404 B2 | 8/2016 | Curtis et al. | |
| 9,434,857 B2 | 9/2016 | Ou | |
| 9,511,034 B1 | 12/2016 | Garrett | |
| 9,642,949 B2 | 5/2017 | Hai et al. | |
| 9,649,650 B2 * | 5/2017 | Werner | B05B 11/3069 |
| 9,655,917 B2 | 5/2017 | Hai et al. | |
| 9,764,099 B2 | 9/2017 | Rimsa et al. | |
| 10,219,793 B2 | 3/2019 | Quintero et al. | |
| 10,441,947 B2 | 10/2019 | Ou | |
| 2001/0011162 A1 | 8/2001 | Epstein | |
| 2001/0019721 A1 * | 9/2001 | Brandt | A61P 43/00 424/443 |
| 2002/0076260 A1 | 6/2002 | Heusser | |
| 2002/0193879 A1 | 12/2002 | Seder et al. | |
| 2003/0044451 A1 | 3/2003 | Mcghee et al. | |
| 2003/0077316 A1 | 4/2003 | Nichols et al. | |
| 2003/0082223 A1 * | 5/2003 | Healy | A61K 8/898 424/401 |
| 2003/0183651 A1 * | 10/2003 | Greer, Jr. | B01F 13/002 222/129 |
| 2004/0004088 A1 * | 1/2004 | Yerby | B65D 83/46 222/145.5 |
| 2004/0181943 A1 | 9/2004 | Kwiecien | |
| 2005/0020844 A1 | 1/2005 | Nelson | |
| 2005/0029296 A1 * | 2/2005 | Hansen | A47L 13/00 222/145.5 |
| 2005/0048124 A1 | 3/2005 | Sarangapani | |
| 2005/0127119 A1 | 6/2005 | Keller | |
| 2005/0182443 A1 | 8/2005 | Jonn et al. | |
| 2005/0256573 A1 | 11/2005 | Seder et al. | |
| 2006/0009099 A1 | 1/2006 | Jonn et al. | |
| 2006/0134313 A1 | 6/2006 | Guggenbichler et al. | |
| 2007/0043332 A1 | 2/2007 | Malcolm et al. | |
| 2007/0104665 A1 * | 5/2007 | Jones | A61K 8/06 424/62 |
| 2007/0293820 A1 | 12/2007 | Dacquay | |
| 2008/0054020 A1 * | 3/2008 | Pierson | A61C 5/64 222/135 |
| 2008/0275403 A1 | 11/2008 | Maaskamp et al. | |
| 2009/0004246 A1 | 1/2009 | Woolfson et al. | |
| 2009/0026660 A1 | 1/2009 | Nelson et al. | |
| 2009/0076480 A1 | 3/2009 | Pudleiner et al. | |
| 2009/0108021 A1 * | 4/2009 | Hansen | C12N 15/8247 222/1 |
| 2010/0280547 A1 | 11/2010 | D'Alessio et al. | |
| 2010/0330025 A1 | 12/2010 | Messersmith et al. | |
| 2011/0027753 A1 | 2/2011 | Maurat et al. | |
| 2011/0091669 A1 | 4/2011 | Tang et al. | |
| 2011/0143148 A1 | 6/2011 | Butts et al. | |
| 2011/0272433 A1 * | 11/2011 | Vogt | B05C 17/00553 222/137 |
| 2012/0237461 A1 | 9/2012 | Yu et al. | |
| 2012/0328787 A1 | 12/2012 | Marrot et al. | |
| 2013/0004586 A1 | 1/2013 | Vachon et al. | |
| 2013/0059109 A1 * | 3/2013 | Kretschmann | C08L 83/04 428/76 |
| 2013/0122314 A1 | 5/2013 | Ou | |
| 2013/0123720 A1 * | 5/2013 | Lind | A61K 47/06 604/310 |
| 2013/0150828 A1 | 6/2013 | Conway | |
| 2013/0171265 A1 | 7/2013 | Saxena et al. | |
| 2013/0310780 A1 | 11/2013 | Phillips | |
| 2013/0310781 A1 | 11/2013 | Phillips et al. | |
| 2014/0221522 A1 | 8/2014 | Antoni et al. | |
| 2015/0159066 A1 | 6/2015 | Hartwell et al. | |
| 2016/0120706 A1 | 5/2016 | Collinson et al. | |
| 2016/0220497 A1 | 8/2016 | Caprasse et al. | |
| 2016/0354172 A1 | 12/2016 | Krogman et al. | |
| 2017/0224823 A1 | 8/2017 | Blanda et al. | |
| 2018/0030327 A1 | 2/2018 | Zhang et al. | |
| 2018/0163090 A1 | 6/2018 | Ou | |
| 2018/0338945 A1 * | 11/2018 | Sambasivam | A61P 31/04 |
| 2019/0001019 A1 | 1/2019 | Lindgren et al. | |
| 2020/0172740 A1 | 6/2020 | Ou et al. | |
| 2021/0369258 A1 * | 12/2021 | Ou | A61B 17/00491 |
| 2021/0369276 A1 * | 12/2021 | Ou | A61L 24/02 |
| 2021/0369639 A1 * | 12/2021 | Ou | A61K 31/444 |
| 2021/0371190 A1 * | 12/2021 | Ou | A61L 24/0026 |
| 2021/0371596 A1 * | 12/2021 | Ou | C08G 77/08 |
| 2021/0371658 A1 * | 12/2021 | Ou | A61L 15/24 |
| 2021/0371662 A1 * | 12/2021 | Ou | C08K 5/5415 |

FOREIGN PATENT DOCUMENTS

| | | |
|---|---|---|
| CN | 106009688 A | 10/2016 |
| EP | 3388037 A1 | 10/2018 |
| JP | 11349897 A | 12/1999 |
| KR | 20160039498 A | 4/2016 |
| WO | 9725085 A1 | 7/1997 |
| WO | 2010128855 | 11/2010 |

(56) References Cited

FOREIGN PATENT DOCUMENTS

| WO | 2013/074732 A1 | 5/2013 |
|---|---|---|
| WO | 2016094084 A1 | 6/2016 |
| WO | 2017158340 A1 | 9/2017 |

OTHER PUBLICATIONS

International Search Report issued in corresponding International Application No. PCT/IB2021/054531, dated Aug. 18, 2021, 4 pages.

Results of a keyword search conducted on Google Scholar using the search terms "antimicrobial AND silicone AND elastomer", https://scholar.google.com, search conducted on Dec. 18, 2021, 2 pages.

International Search Report dated Aug. 13, 2021 for International Application No. PCT/IB2021/054533.

International Search Report dated Aug. 18, 2021 for International Application No. PCT/IB2021/054531.

International Search Report dated Feb. 21, 2020 for International Application No. PCT/IB2019/060233.

International Search Report dated Feb. 21, 2020 for International Application No. PCT/IB2019/060235.

International Search Report dated Jan. 11, 2022 for International Application No. PCT/IB2021/054534.

International Search Report dated Jul. 29, 2021 for International Application No. PCT/IB2021/054515.

International Search Report dated Jul. 30, 2021 for International Application No. PCT/IB2021/054518.

Results of a search conducted for patent referencce U.S. Pat. No. 20200172740 on InnovationQ Plus—IP.com, https://iq.ip.com/discover, search conducted on Dec. 18, 2021, 1 page.

L.N. Lewis, et al ., The chemistry of fumarate and maleate inhibitors with platinum hydrosilylation catalysts, Journal of Organometallic Chemistry, 1996, pp. 221-227, vol. 521.

* cited by examiner

SYSTEMS, METHODS AND DEVICES FOR AEROSOL SPRAYING OF SILICONE BASED TOPICAL SKIN ADHESIVES FOR SEALING WOUNDS

CROSS-REFERENCE TO RELATED APPLICATIONS

The present patent application is related to the following commonly assigned United States patent applications, which were all filed on May 28, 2020: U.S. patent application Ser. No. 16/885,413, U.S., patent application Ser. No. 16/885,361, U.S. patent application Ser. No. 16/885,366, and U.S. patent application Ser. No. 16/885,375. The disclosures of all of the above-identified United States patent applications are hereby incorporated by reference herein.

BACKGROUND OF THE INVENTION

Field of the Invention

The present patent application is generally related to wound closure, and is more specifically related to systems, devices, and methods for applying topical skin adhesives to close wounds.

Description of the Related Art

There are many different methodologies for closing wounds, which typically result from accidental lacerations (i.e., cuts) and surgical incisions. Some of these methods include using sutures, using surgical staples, using surgical skin tapes, and using adhesive compositions that are applied to skin.

Sutures are generally recognized as providing adequate wound support for the duration of wound healing, however, suturing involves additional trauma to the wound because the needle and suture material must pass through the tissue at the margins of the wound. Suturing can also cause cosmetically unattractive wound closure marks and can be time consuming. In addition, depending upon the techniques and types of sutures that are used, sutures may need to be removed at a later date, which could require further medical attention and cause more pain and trauma to a patient.

Surgical staples have many of the disadvantages that are described above for sutures, such as the formation of cosmetically unattractive wound closure marks. Removing staples can be painful and, depending on the location and the patient's pain threshold, may require the use of topical anesthesia. Recently, absorbable staples have been developed that are absorbed by the patient's body over time and do not have to be removed.

Skin closure strips, such as conventional adhesive bandages, are typically utilized for closing relatively superficial skin wounds, however, their use is limited to only certain types and degrees of wounds. The contact adhesives that are used with skin closure strips typically retain holding power for no more than a day or two and can lose holding power quickly in the presence of moisture (e.g., perspiration).

Adhesive compositions, such as topical skin adhesives, are applied directly to tissue and skin for closing wounds. For example, monomer and polymer adhesives are used in medical applications. Since the discovery of the adhesive properties of such monomers and polymers, they have found wide use in medical applications due to the speed with which they cure, the strength of the resulting bond formed, and their relative ease of use.

U.S. Pat. No. 10,219,793, assigned to Ethicon, Inc. of Somerville, N.J., discloses a delivery system for applying topical skin adhesives to skin. The delivery system includes a squeezable container that holds a flowable substance, which is used as a topical skin adhesive. The squeezable container has a sealed proximal end, a sealed distal end having a dispensing neck, and an outer wall that surrounds a storage reservoir. The delivery system has a container support frame assembled with the squeezable container. The container support frame has a proximal edge secured to the sealed proximal end of the squeezable container, a distal edge secured to the dispensing neck of the squeezable container, and first and second lateral edges extending between the proximal and distal edges and overlying opposing sides of the squeezable container. The proximal and distal edges and the first and second lateral edges define a central opening of the container support frame that provides access to the outer wall of the squeezable container. The container support frame has an elongated handle that extends proximally from the proximal edge of the container support frame, which can be used to spread the dispensed topical skin adhesive over skin.

One widely used topical skin adhesive product is sold by Johnson & Johnson Corporation of New Brunswick, N.J. under the trademark DERMABOND® adhesive. Johnson & Johnson's DERMABOND® PRINEO® Skin Closure System includes a mesh having a pressure sensitive adhesive and a polymerization initiator disposed on the mesh. The mesh is applied onto the skin over a wound, and a polymerizable cyanate acrylate based adhesive is applied on the mesh, which bonds the mesh to the skin.

Silicone-based compositions have been used as over-the-counter (OTC) scar reduction products. Silicone-based products used for scar reduction are known for being inert, reducing skin reactions, and improving a patient's post-operative cosmetic appearance. It has been observed, however, that the bonding forces between silicone-based scar gel products and skin surfaces are weak, which results in minimal or no structural bonding being formed between the silicone-based composition and the skin. As a result of the weak bonding forces, silicone-based compositions are easily removed from the skin.

A particularly difficult challenge for medical personnel is closing wounds that are near moveable body parts. When a topical skin adhesive is applied to close a wound that overlies a moveable body part, post-operative motion of the body part will generally compromise the quality of the wound closure. As a result, applying adhesives onto moving body parts introduces additional obstacles for medical personnel seeking effective wound closure.

Thus, in spite of the above-noted advances in wound closure systems and topical skin adhesives, there remains a need for improved topical skin adhesives that can be used to effectively close wounds in skin that covers moveable body parts such as joints, knees, elbows, wrists, etc.

There also remains a need for improved wound closure systems and topical skin adhesives that provide for more stretching, flexibility, and joint articulation when applied to skin that covers moveable body parts.

In addition, there remains a need for topical skin adhesives for use on moveable body parts that have both elasticity and sealing properties to provide watertight closures that prevent post-operative infections and enable proper healing.

Furthermore, there remains a need for improved skin closure systems and topical skin adhesives that hold the dissection applied lengthwise or longitudinally along a joint or a moving body part.

SUMMARY OF THE INVENTION

In one embodiment, an applicator device such as an aerosol spray container is preferably adapted to spray an aerosol mist of a silicone-based topical skin adhesive onto skin to provide a watertight closure for healing wounds and preventing post-operative infections.

In one embodiment, the sprayable, silicone-based topical skin adhesive provides both elasticity and sealing properties for sealing wounds in skin that covers and/or overlies moveable body parts.

In one embodiment, at normal body temperatures, the silicone-based topical skin adhesive is preferably adapted to cure on skin in less than eight minutes.

In one embodiment, the skin holding forces that are formed between the silicone-based topical skin adhesive disclosed herein and skin is better than the results that may be attained when using a cyanate acrylate adhesive, which are a family of fast-acting adhesives with medical and industrial uses.

In one embodiment, an aerosol spray device preferably includes a container with first and second fluid reservoirs disposed therein that are divided from one another. In one embodiment, the first fluid reservoir desirably holds a first mixture including a first aerosol propellant and a first part of a silicone based topical skin adhesive that is dissolved in the first aerosol propellant, and the second fluid reservoir desirably holds a second mixture including a second aerosol propellant and a second part of the silicone based topical skin adhesive that is dissolved in the second aerosol propellant.

In one embodiment, an aerosol spray dispensing system is preferably connected with the container, which is configured to combine the first and second mixtures to form the silicone based topical skin adhesive and dispense the silicone based topical skin adhesive from the container as an aerosol spray.

In one embodiment, one of the first and second mixtures may include a catalyst that is adapted to precipitate a chemical reaction between the first and second parts of the silicone based topical skin adhesive.

In one embodiment, the catalyst is preferably a novel platinum catalyst for use with cross-linkable silicone coatings. In one embodiment, the catalyst comprises a platinum tetramethyldivinyl disiloxane diethyl maleate complex having the following formula:

$$Pt[(CH_2\!\!=\!\!CH)(CH_3)_2Si]_2O\cdot(COCH\!\!=\!\!CHCO)(C_2H_5O)_2.$$

In one embodiment, the first part of the silicone based topical skin adhesive preferably includes a vinyl-terminated polydimethylsiloxane polymer, and the second part of the silicone based topical skin adhesive preferably includes a vinyl-terminated polydimethylsiloxane polymer.

In one embodiment, the first mixture may include first silica particles homogenously dispersed in the first aerosol propellant, and the second mixture may include second silica particles homogenously dispersed in the second aerosol propellant.

In one embodiment, the second mixture desirably includes a chain extender mixed with the second part of the silicone based topical skin adhesive. In one embodiment, the chain extender may include silicon hydride (SiH) terminated polydimethylsiloxane.

In one embodiment, the first and second aerosol propellants are desirably low boiling point hydrocarbon compounds. In one embodiment, the low boiling point hydrocarbon compounds may include hexane, pentane, butane, isobutene, propane, fluorinated solvents including 1,1-difluoroethane and Solstice® Performance Fluid, ethers including dimethyl ether and diethyl ethyl, and mixtures or combinations thereof.

In one embodiment, the aerosol spray dispensing system may include a dispensing nozzle connected with an upper end of the container for dispensing the aerosol spray of the silicone based topical skin adhesive, and a dip tube disposed inside the container having an upper end in fluid communication with the dispensing nozzle, and a lower end having a first opening in fluid communication with the first fluid reservoir and a second opening in fluid communication with the second fluid reservoir. The aerosol spray dispensing system may also include a fluid control valve located inside the container between the dip tube and the dispensing nozzle, and a static mixer extending between the dip tube and the valve for combining the first and second mixtures together to form the silicone based topical skin adhesive.

In one embodiment, an aerosol spray device preferably includes a container having first and second fluid reservoirs disposed therein that are isolated from one another.

In one embodiment, the first fluid reservoir desirably holds a first mixture including a first aerosol propellant, a first part of a silicone based topical skin adhesive that is dissolved in the first aerosol propellant, and first silica particles homogeneously dispersed in the first aerosol propellant.

In one embodiment, the second fluid reservoir desirably holds a second aerosol propellant, a second part of the silicone based topical skin adhesive that is dissolved in the second aerosol propellant, and second silica particles homogeneously dispersed in the second aerosol propellant.

In one embodiment, the aerosol spray device preferably includes an aerosol spray dispensing system that is connected with the container, which is configured to combine the first and second mixtures for forming the silicone based topical skin adhesive and dispensing the silicone based topical skin adhesive from the container as an aerosol spray.

In one embodiment, the first silica particles are preferably include first silica fume particles homogenously dispersed in the first propellant, and the second silica particles preferably include second silica fume particles homogenously dispersed in the second propellant.

In one embodiment, the second mixture may include a cross-linker and a chain extender mixed with the second part of the silicone based topical skin adhesive. In one embodiment, the cross-linker may include polymethyl hydro siloxane. In one embodiment, the chain extender may include SiH terminated polydimethylsiloxane.

In one embodiment, the aerosol spray dispensing system preferably includes a dispensing nozzle connected with an upper end of the container, a dip tube disposed inside the container having an upper end in fluid communication with the dispensing nozzle, and a lower end having a first opening in fluid communication with the first fluid reservoir and a second opening in fluid communication with the second fluid reservoir, a fluid control valve located inside the container and being located between the upper end of the dip tube and the dispensing nozzle, and a static mixer located between the dip tube and the valve for mixing together the contents of the first mixture of the first fluid reservoir with the contents of the second mixture of the second fluid reservoir.

In one embodiment, an aerosol spray device preferably includes a container having first and second fluid reservoirs disposed therein that are divided from one another. In one embodiment, the first fluid reservoir preferably contains a first mixture including a first part of a silicone based topical skin adhesive, and the second fluid reservoir preferably contains a second mixture including a second part of the silicone based topical skin adhesive.

In one embodiment, an aerosol spray dispensing system is desirably connected with the container. The aerosol spray dispensing system preferably combines (e.g., mixes) the first and second mixtures for forming the silicone based topical skin adhesive and dispenses the silicone based topical skin adhesive from the container as an aerosol spray.

In one embodiment, the first part of the silicone based topical skin adhesive preferably includes a vinyl-terminated polydimethyl silicone polymer, and the first mixture may include a formulation of silica fume particles, a catalyst, low molecular weight vinyl-terminated polydimethyl silicone polymer, and pentane.

In one embodiment, the second part of the silicone based topical skin adhesive preferably includes a vinyl-terminated polydimethyl silicone polymer, and the second mixture may include a formulation of silica fume particles, a polymethyl hydro siloxane cross linker, a SiH terminated polydimethylsiloxane chain extender, and pentane.

In one embodiment, the first part of the silicone based topical skin adhesive preferably includes a vinyl-terminated polydimethyl silicone polymer, and the first mixture further may include a formulation of silica fume particles, a catalyst, low molecular weight vinyl-terminated polydimethyl silicone polymer, and hexane.

In one embodiment the second part of the silicone based topical skin adhesive may include a vinyl-terminated polydimethyl silicone polymer, and the second mixture may include a formulation of silica fume particles, a polymethyl hydro siloxane cross linker, a SiH terminated polydimethylsiloxane chain extender, and hexane.

In one embodiment, the first part of the silicone based topical skin adhesive preferably includes a vinyl-terminated polydimethyl silicone polymer, and the first mixture may include a formulation of silica fume particles, a catalyst, low molecular weight vinyl-terminated polydimethyl silicone polymer, dieehtyl ethyl, and pentane.

In one embodiment, the second part of the silicone based topical skin adhesive preferably includes a vinyl-terminated polydimethyl silicone polymer, and the second mixture may include a formulation of silica fume particles, a polymethyl hydro siloxane cross linker, a SiH terminated polydimethylsiloxane chain extender, diethyl ether, and pentane.

In one embodiment, the silicone-based topical skin adhesive disclosed herein may be stretched up to 160% of its original length and fully recover back to its original, pre-stretched dimension, which provides a tremendous improvement over conventional cyanate acrylate adhesives that are used for wound closure.

Forming a uniform and effective wound dressing with a topically applied adhesive typically requires both rapid mixing of the adhesive followed by rapid spreading over a skin surface. Due to its high viscosity relative to cyanate acrylate based adhesives, uniformly spreading and applying high viscosity, rapidly curing silicone adhesives is uniquely challenging. In particular, the viscosity of silicone is several hundred thousand times higher than the viscosity of conventional cyanate acrylate based topical skin adhesives. The very high viscosity of a silicone-based adhesive makes it much more difficult to mix a silicone-based adhesive than a cyanate acrylate based adhesive. Inadequate mixing of an adhesive, such as a silicone-based adhesive, will lead to poor, incomplete or long duration cure cycles.

In one embodiment, the viscosity of the components of a silicone-based topical skin adhesive may be significantly reduced by dissolving one or more of the components of the silicone-based topical skin adhesive in an organic solvent. Moreover, by reducing the viscosity of the components of a silicone-based topical skin adhesive, the silicone-based adhesive may be sprayed in aerosol form using an aerosol spray device. Thus, in one embodiment, an aerosol spray device including an aerosol spray dispensing system may be used to deliver an aerosol mist of a silicone-based adhesive onto a wound in skin.

In one embodiment, a two-part silicone-based topical skin adhesive is preferably dissolved in low boiling organic solvents, which may include solvents that are commonly referred to as propellants that are used for forming aerosol sprays in the aerosol industry.

In one embodiment, an aerosol spray device may include a container having first and second fluid reservoirs that are separated from one another so that the contents of the first fluid reservoir are isolated from the contents of the second fluid reservoir. In one embodiment, the different components of a two-part silicone based topical skin adhesive may be held in the separate first and second fluid reservoirs inside the aerosol container (e.g., an aerosol spray can).

In one embodiment, a propellant preferably includes liquefied and/or dissolved gases that are immiscible with one or more of the components of the silicone-based topical skin adhesive.

In one embodiment, liquefied and/or dissolved gases are desirably retained in substantially a liquid phase of the effervescent composition with a slow boiling occurring at temperatures that are significantly higher than the boiling points of the liquefied and/or dissolved gases at the prevailing environmental pressure.

In one embodiment, an aerosol spray device preferably includes a dip tube that directs the components of the two-part silicone adhesive into a static mixer that combines the components together, whereupon the mixtures travels downstream to a valve. In one embodiment, when the pressure is released outside the valve (e.g., by depressing a dispensing nozzle), the contents of the pressurized container are preferably discharged and any liquefied and/or dissolved gas propellants that are discharged from the container vaporize almost instantaneously as the liquefied and/or dissolved gases enter a much lower pressure zone (i.e., atmospheric pressure) that is located outside of the container, which provides an aerosol mist or aerosol spray of a silicone-based topical skin adhesive that uniformly covers an area of skin (e.g., to close a wound in the skin).

In one embodiment, an aerosol spray device may include a conventional spray bottle or a spray can. In one embodiment, an aerosol spray device may have a charging bulb that is adapted to be squeezed for dispensing a mist of the silicone-based topical skin adhesive.

In one embodiment, silica filler particles (e.g., silica fume) may be homogeneously dispersed into a low boiling point propellant, so that the mixed silicone-based topical skin adhesive may easily pass through the aerosol spray dispensing system (e.g., the valve and the dispensing nozzle) to form uniform adhesive layers on areas of skin. The silica filler particles preferably facilitate passage of the two-part silicone based topical skin adhesive through the fluid path of the aerosol spray dispensing system, which may include a dip tube, a static mixer, a valve, and a dispensing nozzle.

In one embodiment, providing an aerosol spray device that is capable of spraying an aerosol mist of a two-part silicone based topical skin adhesive makes it much easier for patients to treat themselves at home after the initially applied layer of the topical skin adhesive layer has fallen off. Thus, the aerosol spray device and the unique formulas for the two-part silicone based topical skin adhesives enable patients to apply a silicone-based topical skin adhesive outside a traditional operating room setting, which will provide better wound recovery for patients.

DETAILED DESCRIPTION OF PREFERRED EMBODIMENTS

Figure 1:
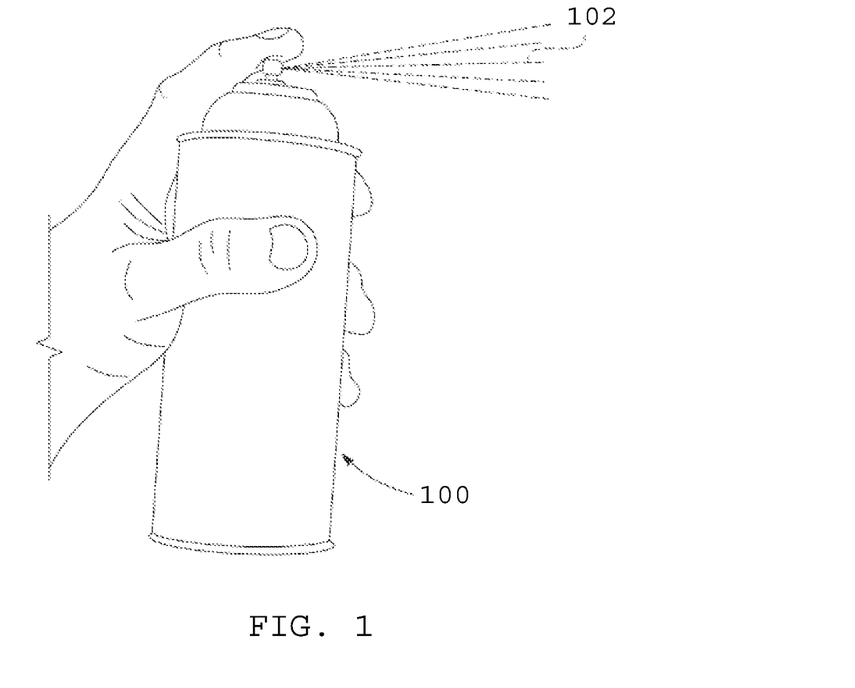
FIG. 1 is a side view of an aerosol spray device for supplying an aerosol mist of a two-part silicone based topical skin adhesive, in accordance with one embodiment of the present patent application.

Referring to FIG. 1, in one embodiment, an aerosol spray device 100 is utilized to dispense a two-part silicone based topical skin adhesive as an aerosol mist 102 that contains liquid particles of the adhesive. The aerosol mist 102 of the adhesive may be applied to skin for closing a wound.

Figure 2:
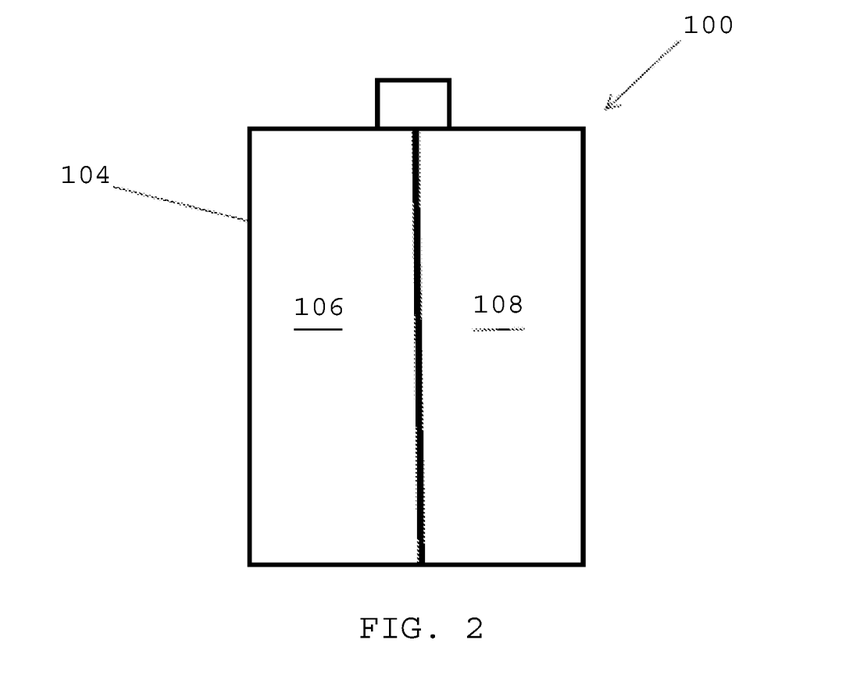
FIG. 2 is a schematic, cross-sectional view of the aerosol spray device shown in FIG. 1.

Referring to FIG. 2, in one embodiment, the aerosol spray device preferably includes a container 104 having a first fluid reservoir 106 and a second fluid reservoir 108 that is separated and/or isolated from the first fluid reservoir 106. The first and second fluid reservoirs 106, 108 are desirably disposed inside the container 104. In one embodiment, a first part of a two-part silicone based topical skin adhesive is disposed in the first fluid reservoir 106 and a second part of a two-part topical skin adhesive is disposed in the second fluid reservoir 108

Figure 3:
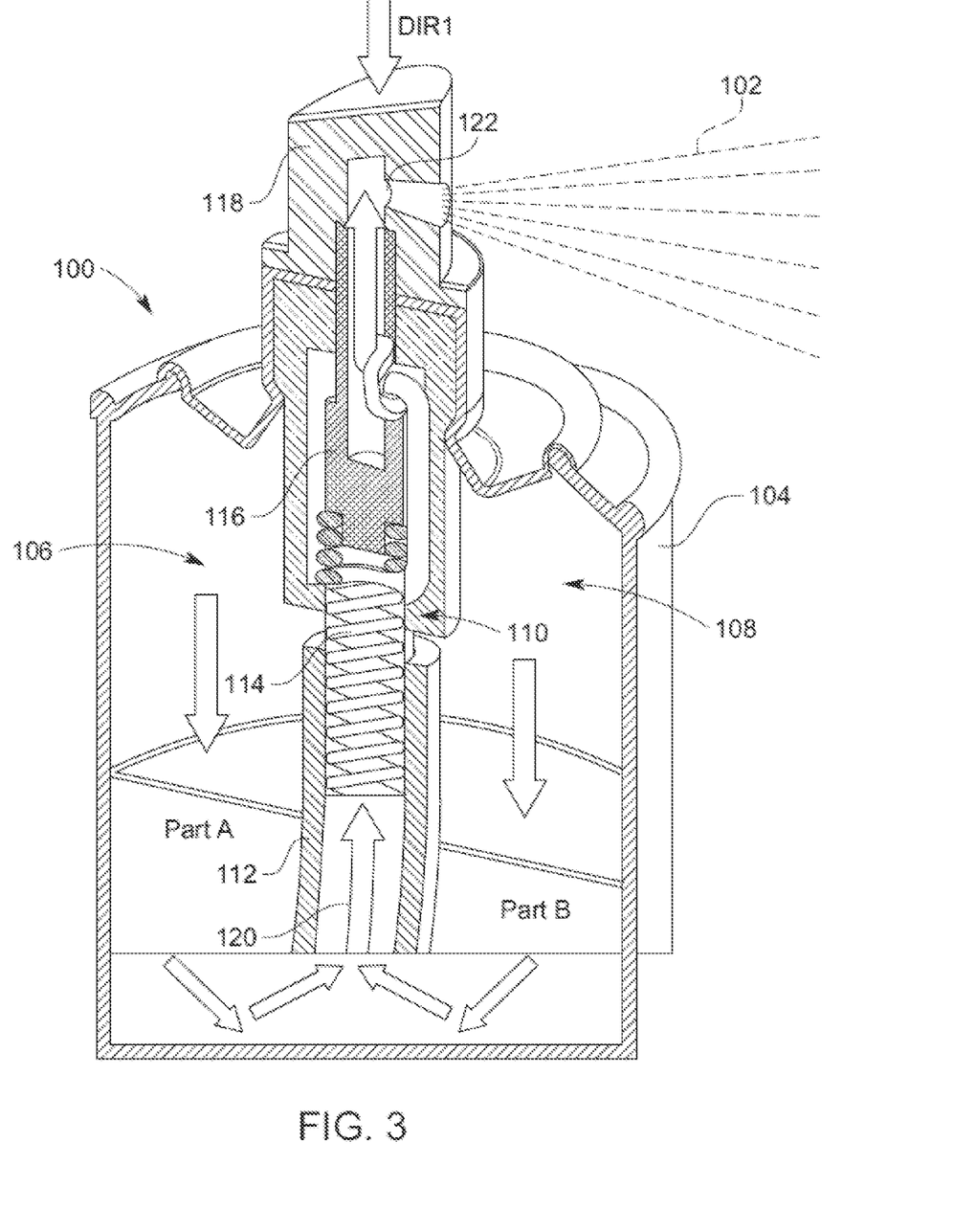
FIG. 3 is a schematic, cross-sectional view of the aerosol spray device shown in FIG. 1.

Referring to FIG. 3, in one embodiment, the aerosol spray device 100 preferably includes an aerosol spray dispensing system 110 that is configured to dispense a two-part silicone based topical skin adhesive as an aerosol mist. In one embodiment, the aerosol spray dispensing system 110 preferably includes a dip tube 112 disposed inside the container 104, a static mixer 114 located downstream from the dip tube 112, a valve 116 located downstream from the static mixer 114, and a dispensing nozzle 118 located downstream from the valve. In one embodiment, the aerosol spray dispensing system defines a fluid flow path 120 that extends through the dip tube 112, the static mixer 114, the valve 116, and the dispensing nozzle 118. In one embodiment, the dispensing nozzle 118 may be depressed in the direction DIR1 for opening the valve 116, which creates low pressure at the top of the container 104 for drawing the fluid components of the two-part silicone based topical skin adhesive into a lower end of the dip tube 112, mixing the components together within the static mixer 114, and enabling the mixed components to pass through the valve 116 for being dispensed from the dispensing nozzle 118 as a fine mist 102.

In one embodiment, the aerosol spray device 100 is preferably designed to create and dispense a silicone-based topical skin adhesive as an aerosol mist of liquid particles. In one embodiment, the container 104 of the aerosol spray device 100 preferably holds a first part (Part A) of a two-part silicone based topical skin adhesive and a first aerosol propellant under pressure in the first fluid reservoir 106, and a second part (Part B) of the two-part silicone based topical skin adhesive and a second aerosol propellant under pressure in the second fluid reservoir 108. The first and second aerosol propellants are preferably organic solvents that lower the viscosities of the first and second parts of the silicone adhesive, respectively, and also produce pressurized gases that propel the first and second parts (Parts A and B) of the silicone adhesive from the container 104.

In one embodiment, when the valve 116 of the aerosol spray device 100 is opened, the silicone based topical skin adhesive is forced out of a small hole 122 in the dispensing nozzle 118 and emerges as an aerosol or mist that may be applied to a skin surface as a topical skin adhesive. As the first and second propellants expand to drive out the respective first and second parts of the silicone adhesive, some of the first and second propellants evaporate inside the container 100 to maintain a constant pressure. Outside the container 100, the droplets of the first and second propellants evaporate rapidly, leaving the silicone-based adhesive suspended as very fine particles or droplets 102.

In one embodiment, a first part of the two-part silicone topical skin adhesive is dissolved in a first low boiling point organic solvent (i.e., referred to as a propellant in the aerosol industry) and charged into the first fluid reservoir 106 disposed inside the container 104 of the aerosol spray device 100.

In one embodiment, a second part of the two-part silicone topical skin adhesive is dissolved in a second low boiling point organic solvent and charged into the second fluid reservoir 108 disposed inside the container 104 of the aerosol spray device 100.

The first and second fluid reservoirs 106, 108 (FIG. 2) are preferably divided from one another (i.e., sealed from one another) so that the contents within the first and second fluid reservoirs 106, 108 remain separate and apart from one another until the valve 116 is opened to mix the two parts of the silicone adhesive together.

In one embodiment, the propellants in the first and second fluid reservoirs 106, 108 may include liquefied and/or dissolved gases immiscible with the components of the silicone topical skin adhesive. The liquefied and/or dissolved gases may be retained essentially completely in the liquid phase of the effervescent composition with a slow boiling occurring at temperatures which are significantly higher than the boiling points of the liquefied and/or dissolved gases at the prevailing environmental pressure.

In one embodiment, the first and second propellants may include organic solvents. In one embodiment, the organic solvents may include low boiling point hydrocarbon compounds, including, but not limited to, hexane, pentane, butane, isobutane and propane, or fluorinated solvent such as 1,1-difluoroethane and Solstice® PF, or ether such as dimethyl ether and diethyl ethyl, and mixtures thereof, which are commonly use in aerosol cans.

In one embodiment, upon activation of the aerosol spray device, the two-part components of the silicone adhesive are preferably mixed by the internal static mixer 114 and passed into the valve 116. In one embodiment, when the valve 116 is opened for releasing pressure, the contents of the pressurized container 104 are discharged and the propellants discharged from the container vaporize as they enter atmospheric pressure outside the container 104.

In one embodiment, the aerosol spray device may include a conventional spray bottle.

In one embodiment, silica filler particles (e.g., silica fume) may be homogeneously dispersed into the first and second propellants contained within the respective first and second fluid reservoirs so that the contents of the first and second fluid reservoirs may easily pass through the valve 116 and the spray nozzle 118 of the aerosol spray device 100.

The aerosol spray device 100 disclosed herein makes it easy for patients to treat themselves at home by using the device to re-apply the silicone topical skin adhesive over a wound at home. Thus, after the initial silicone adhesive falls off, a patient may spray a new layer of silicone adhesive onto skin for sealing a wound, which extends the use of topical skin adhesives beyond the traditional operating room use of surgical adhesives. Providing a silicone topical skin adhesive in aerosol form will expand the benefits provided by the class of adhesives and affords better wound recovery for patients.

In one embodiment, a two-part silicone based topical skin adhesive that may be sprayed as an aerosol spray or aerosol mist may include one or more formulations.

In one embodiment, one of the parts of the two part silicone based topical skin adhesive may include a catalyst for precipitating a chemical reaction between the two parts of the silicone adhesive.

Karstedt of GE Silicone invented a highly active platinum catalyst at the beginning of the 1970's, which was disclosed in U.S. Pat. No. 3,775,452. Vinyl terminated polydimethylsiloxane can react with polymethylhydrosiloxane containing cross linker in less than 1 minute at ambient temperature with as little as 10 ppm of the Karstedt catalyst. The traditional platinum catalyst does not enable the reaction between OH groups on the surface of silica particles reacts and the OH functions on the surface of substrate. This type of condensation reaction tends to be slow at ambient condition and the typical catalyst for this reaction including organic amine and catalyst such as tin dilaurate. Trace amount of condensation catalyst will terminate the catalytic ability of platinum catalyst which is referred as platinum poisoning in the silicone industry. A novel platinum comparable catalyst is needed to activate the OH condensation between silica particle and substrate material, to enable rapid adhesion formation between silicone and a given substrate material. A platinum based novel catalyst of the present invention is able to activate both vinyl silylation and OH condensation simultaneously.

The novel catalyst disclosed in the present patent application is prepared by reacting Karstedt's catalyst with diethyl maleate according to Scheme 1. The novel platinum tetramethyldivinyl disiloxane diethyl maleate catalyst enables both vinyl silylation and a condensation reaction. This is referred to as a "dual functional silicone catalyst".

Scheme 1

The novel catalyst disclosed in the present patent application may be prepared in the following manner: a Karstedt catalyst in xylene solution is mixed with diethyl maleate at ambient temperature for a sufficiently effective time to complete the reaction, e.g., 10 hours.

The resulting catalyst solution containing the novel catalyst of the present patent application is ready to use in a composition useful as a topical skin adhesive. The formula of the resulting platinum complex catalyst (platinum tetramethyldivinyl disiloxane diethyl maleate complex) is:

It should be noted that the resulting catalyst reaction mixture will contain a small amount of the reaction product divinyltetramethyldisiloxane. This component does not affect the catalyst and is a low boiling point component that is rapidly evaporated. Accordingly, purification of the catalyst mixture to remove divinyltetramethyldisiloxane is optional, and it is believed that its presence at ultra low concentrations will not affect the cross-linking reaction of a cross-linkable silicone polymer. The novel catalyst of the present invention also actives the bonding formation between silanol groups on the surface of silica fillers and OH functions on a given surface, that is, the catalyst is capable to activate two reactions. This allows for curing the cross-linkable components in silicone coatings to rapidly form coating films at desired curing temperatures and provides bonding to a given substrate such as human skin.

Example 1. Novel Platinum Catalyst (Synthesis Procedure)

44.50 g of Gelest SIP 6831.2 (2.2% platinum divinyl tetramethyldisiloxane complex in xylene, Karstedt catalyst) was mixed with 2 g of diethyl maleate for 24 hours at ambient temperature. Samples were taken out after 3 hours, 18 hours, and 24 hours for NMR testing and the NMR spectra for the 3 hour sample is shown in FIG. 4.

The formation of the novel catalyst is the evidence for Scheme 1, which rests on NMR spectroscopic identification. Karstedt catalyst is known with a characteristic $^{195}$Pt signal at approximately −6111 ppm.

Figure 4:
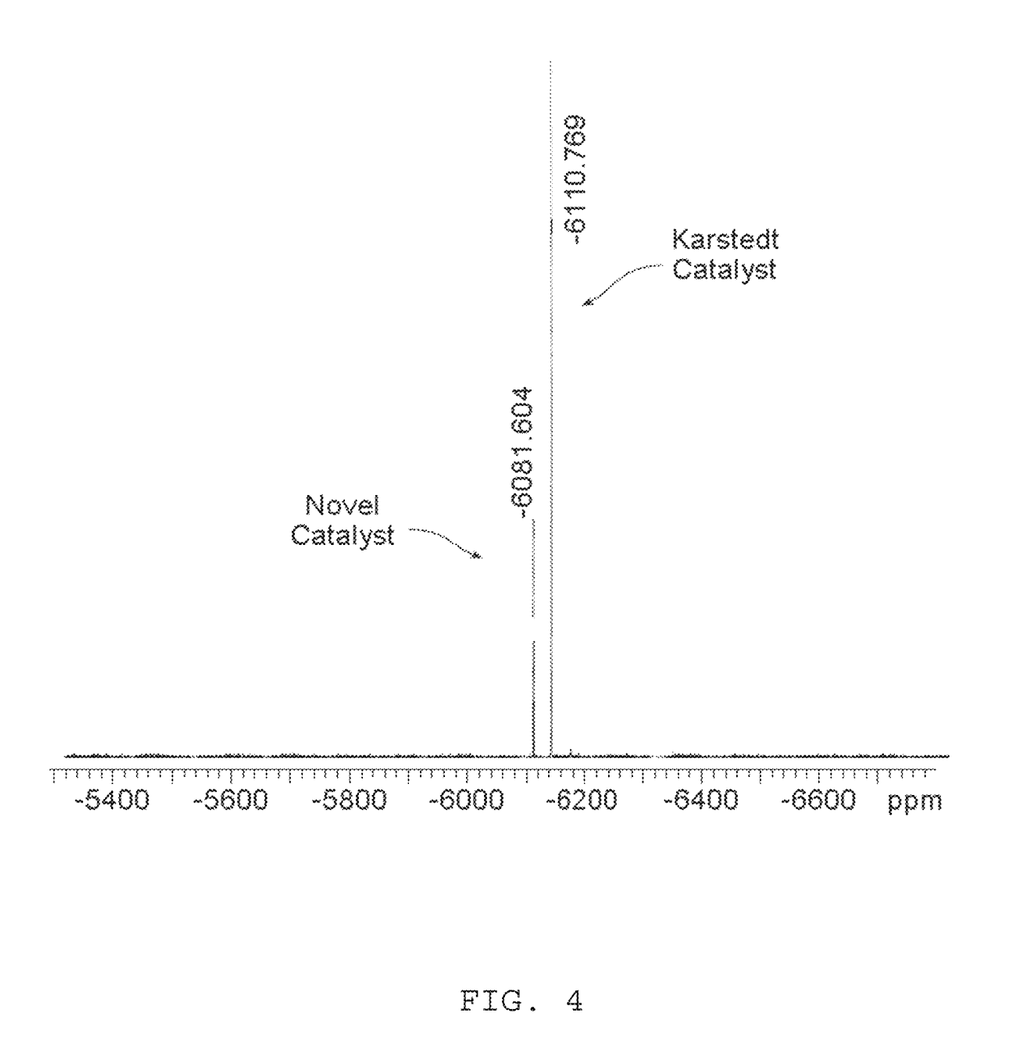
FIG. 4 is an NMR peak comparison of the Karstedt Catalyst compared with the NMR peak of the novel catalyst of this invention.

After 3 hours of mixing of the mixtures of Example 1, a new $^{195}$Pt signal at −6082 ppm was observed along with the original signal for the Karstedt catalyst at −6111 ppm as illustrated in the NMR spectra of this mixture at 3 hours in FIG. 4. The intensity of the new signal increases over time while the intensity of the Karstedt catalyst signal reduced at the same time.

The silicone compositions disclosed in the present patent application cure in several minutes to films that are neither sticky nor tacky. In contrast and as would be appreciated by one of skill in the art, some silicone adhesives, such as silicone pressure sensitive adhesives (PSA's), are by nature sticky or tacky and are intended to be such for the entire usable life of the adhesive. Such useable life of the tacky silicone PSA's may be upwards to several years. The non-tackiness of the compositions and examples of this invention is measured by ASTM C679.

In general ASTM C679 consists of lightly touching a surface of a curing sealant with a polyethylene film at regular intervals until the sealant does not attach itself to the film and the film appears clean when peel from the surface. More specifically a strip of polyethylene film is placed on the surface of the curing elastomer and a 30 g weight is placed on the film. The weight is left in place for 30 seconds, then removed and the polyethylene strip is removed and examined for sealant attachment to the film. The length of time from when the sealant was first applied onto a given surface until the time the sealant is no longer picked up by the film is called tack-free time and is the time point at which the film exhibits a non-tacky nature which evidences that the sealant has cured.

In one embodiment, a two-part silicone based topical skin adhesive adapted to be sprayed as an aerosol mist may be formulate as set forth in Example 2 below.

Example 2. Preparation of a Sprayable Silicone Based Topical Skin Adhesive Using Silica Containing Silicone Raw Material In one embodiment, the silicone based topical skin adhesive preferably has a first part (i.e., Part A) and a second part (i.e., Part B) that are mixed together to form the silicone based topical skin adhesive.

Part A. In one embodiment, Part A includes 9 g of a base material containing vinyl-terminated polydimethyl silicone base polymer and silica fume particles, which are mixed with 0.51 g of the Catalyst described above, 0.9 g of low molecular weight vinyl-terminated polydimethyl silicone base polymer (e.g., Gelest DMS V21), and 27 g of pentane (i.e., a first propellant) using a high speed centrifugal mixer (e.g., FlackTek DAC150 FV-K) at approximately 3470 rpm for three minutes.

Part B. In one embodiment, Part B of a base material containing vinyl-terminated polydimethyl silicone base polymer and silica fume particles, which are mixed with 0.81 g of polymethyl hydro siloxane (i.e., a cross linker) such as Gelest DMS H991, 0.27 g of SiH terminated polydimethylsiloxane (i.e., a chain extender) such as Gelest DMS H21, and 24.3 g of pentane (i.e., a second propellant) using a high speed centrifugal mixer (FlackTek DAC150 FV-K) at 3470 rpm for three minutes.

In one embodiment, a two-part silicone based topical skin adhesive adapted to be sprayed as an aerosol mist may be formulate as set forth in Example 3 below.

Example 3. Preparation of Sprayable Silicone Based Topical Skin Adhesive Using Silica Containing Silicone Raw Material In Example 3, the silicone based topical skin adhesive preferably has a first part (i.e., Part A) and a second part (i.e., Part B) that are mixed together to form the silicone based topical skin adhesive.

Part A. In one embodiment, Part A of a base material containing 9 g of vinyl-terminated polydimethyl silicone base polymer and silica fume particles are preferably mixed with 0.51 g of the Catalyst disclosed in Example 1, 0.9 g of low molecular weight vinyl-terminated polydimethyl silicone base polymer (e.g., Gelest DMS V21), and 13.5 g of hexane (i.e., the first propellant) using a high speed centrifugal mixer (e.g., FlackTek DAC150 FV-K) at 3470 rpm for three minutes.

Part B. In one embodiment, Part B of a base material containing 8.1 g of vinyl-terminated polydimethyl silicone base polymer and silica fume particles are preferably mixed with 0.81 g of polymethyl hydro siloxane (i.e., a cross linker) such as Gelest DMS H991, 0.27 g of SiH terminated polydimethylsiloxane (i.e., a chain extender) such as Gelest DMS H21, and 12.2 g of hexane (i.e., the second propellant) using a high speed centrifugal mixer (e.g., FlackTek DAC150 FV-K) at 3470 rpm for three minutes.

In one embodiment, a two-part silicone based topical skin adhesive adapted to be sprayed as an aerosol mist may be formulate as set forth in Example 4 below.

Example 4. Preparation of a Sprayable Silicone Based Topical Skin Adhesive Using Silica Containing Silicone Raw Material In Example 4, the silicone based topical skin adhesive preferably has a first part (i.e., Part A) and a second part (i.e., Part B) that are mixed together to form the silicone based topical skin adhesive, which is dispensed as an aerosol spray.

Part A. In one embodiment, Part A of a base material containing 18 g of vinyl-terminated polydimethyl silicone base polymer and fume silica particles (Elkem 44 experimental base) are preferably mixed with 1.02 g of the Catalyst disclosed in Example 1, 1.8 g of low molecular weight vinyl-terminated polydimethyl silicone base polymer (e.g., Gelest DMS V21), 9 g of diethyl ethyl, and 9 g of pentane (i.e., the first propellant) using a high speed centrifugal mixer (e.g., FlackTek DAC150 FV-K) at 3470 rpm for three minutes.

Part B. In one embodiment, Part B of a base material containing 16.2 g of vinyl-terminated polydimethyl silicone base polymer and silica fume particles (Elkem 44 experimental base) are preferably mixed with 1.62 g of polymethyl hydro siloxane (i.e., a cross linker) such as Gelest DMS H991, 0.54 g of SiH terminated polydimethylsiloxane (i.e., a chain extender) such as Gelest DMS H21, 8.1 g of diethyl ether, and 8.1 g of pentane (i.e., the second propellant) using a high speed centrifugal mixer (e.g., FlackTek DAC150 FV-K) at 3470 rpm for three minutes.

Test specimens were prepared to evaluate the performance of the two-part silicone based topical skin adhesive disclosed herein versus conventional cyanate acrylate based topical skin adhesives. As will be set forth in more detail below, the test specimens were synthetic substrates (e.g., polyester meshes). The two-part silicone based topical skin adhesive was applied to a first group of the test specimens, and the conventional cyanate acrylate based adhesive was applied to a second group of the test specimens. Various tests were performed on both groups of the test specimens to evaluate the performance of the silicone based adhesive versus the conventional cyanate acrylate based adhesive. The various tests included holding strength tests, peel strength tests, and stretch tests.

Example 5. Preparation of the Test Specimens

Holding Strength. Test specimens were prepared for use in conducting holding strength tests. The test specimens were made from a polyester mesh substrate having a thickness of 0.05 inches (e.g., Dura-Lar® film sold by Graphic Plastics of Maple Heights, Ohio). The 6×11 inch polyester mesh substrate was cut along a cut line into two halves, each having 3×11 inch dimensions. A two inch wide pressure sensitive adhesive was placed along the cut line to hold the two cut halves together. A first group of test specimens were prepared for evaluating each of the two-part silicone based topical skin adhesives disclosed in Examples 2, 3, and 4 of the present patent application. The two-part silicone based topical skin adhesives described above in Example 2, 3, and 4 were applied to different test specimens of the first group of test specimens. Each silicone adhesive that was used consisted of 40 g of a pre-mixed two-part silicone based topical skin adhesive having 20 g of Part A and 20 g of Part B. An aerosol spray device (e.g., a spray bottle) was used to apply an even covering of the silicone adhesive onto the entire area of each test specimen.

The test specimens for Group 1 were dried at about 33 degrees centigrade for approximately six minutes. For each formation of the two-part silicone based topical skin adhesive (i.e., the formulations disclosed in Examples 2, 3 and 4), a first test specimen (e.g., test strip) was prepared for use in a one hour test and a second test specimen was prepared for use in a one day test.

Group 2 Test Specimens. A second group of test specimens (i.e., polyester mesh test strips) were prepared using a cyanate acrylate based topical skin adhesive product.

Peel Strength Test Specimens. Test specimens for conducting peel strength tests were made using polyester mesh substrates having a thickness of 0.05 inches (e.g., Dura-Lar® film sold by Graphic Plastics of Maple Heights, Ohio). The test specimens had 5×5 inch dimensions and were coated with a pressure sensitive adhesive. Each 5×5 polyester mesh substrate was placed on a Mylar substrate having the same 5×5 inch dimensions. For Group 1 test specimens, an aerosol spray device containing 40 g of a pre-mixed two-part silicone topical skin adhesive (e.g., the formulations disclosed in Examples 2, 3, and 4 with 20 g of Part A and 20 g of Part B) was used to apply the two-part silicone based topical skin adhesive onto the test specimens to cover the entire area of the polyester mesh substrates. One inch wide test specimens were cut for testing. After being cut, the test specimens were stored at 33 degrees centigrade for 24 hours.

Group 2 test specimens. A second group of polyester mesh substrates was prepared for use in peel strength tests, using the same steps as outlined above for the Group 1 test specimens, but using the conventional cyanate acrylate based topical skin adhesive rather than the silicone adhesive that was applied to the Group 1 test specimens.

Stretch Test Specimens. The test specimens were 5×5 inch polyester mesh substrates that were coated with a pressure sensitive adhesive and placed on a Teflon substrate. For the Group 1 test specimens, an aerosol spray device was used that contained a pre-mixed two-part silicone based topical skin adhesive (e.g., the formulations disclosed in Examples 2, 3 and 4, with 20 g of Part A and 20 g of Part B). The two-part silicone based topical skin adhesive was applied onto the Group 1 test specimens to evenly cover the entire area of the polyester mesh substrates. After one hour, the silicone coated polyester mesh substrates were peeled off the Teflon substrate. One inch wide silicone coated mesh test specimens were cut for conducting stretch testing.

Group 2 Test Specimens. The Group 2 test specimens were made using a cyanate acrylate based topical skin adhesive product. With the test specimens placed on a Teflon substrate, the cyanate acrylate based topical skin adhesive was applied to the test specimens. After one hour, the cyanate acrylate coated polyester mesh substrates were peeled off the Teflon substrate. One inch wide cyanate acrylate coated mesh test specimens were cut for conducting stretch testing.

Performance Testing.

Holding Strength Testing.

Holding strength tests were performed on the Group 1 test specimens coated with the two-part silicone based topical skin adhesives (i.e., Examples 2, 3, and 4), and the Group 2 test specimens coated with the cyanate acrylate based topical skin adhesive. The test results are summarized below in Table 1.

TABLE 1

| Sample | Holding Strength (lb/in) |
| --- | --- |
| Example 2 (1 hr) | 14.2 |
| Example 2 (1 Day) | 15.3 |
| Example 3 (1 hr) | 12.8 |
| Example 3 (1 Day) | 15.1 |
| Example 4 (1 hr) | 14.7 |

TABLE 1-continued

| Sample | Holding Strength (lb/in) |
| --- | --- |
| Example 4 (1 Day) | 16.9 |
| Cyanate Acrylate (1 hr) | 9.2 |
| Cyanate Acrylate (1 Day) | 10.6 |

Table 1 shows that the holding force for the polyester film substrates coated with the two-part silicone based topical skin adhesive disclosed in the present patent application is substantially higher than can be attained when using polyester film substrates that are coated with the conventional cyanate acrylate based adhesive product.

Peel Strength Test. Peel strength tests were performed on the Group 1 test specimens coated with the two-part silicone based topical skin adhesives (i.e., Examples 2, 3, and 4), and the Group 2 test specimens coated with the cyanate acrylate based topical skin adhesive. The results are summarized below in Table 2.

TABLE 2

| Sample | Average Peel Strength (lb/in) | Maximum Peel Strength (lb/in) |
| --- | --- | --- |
| Example 2 | 2.0 | 3.3 |
| Example 3 | 1.3 | 2.5 |
| Example 4 | 1.4 | 2.7 |
| Cyanate Acrylate | 1.0 | 1.4 |

Table 2 shows that the peel force for the polyester film substrates coated with the two-part silicone topical skin adhesive disclosed in the present patent application is significantly higher than can be attained when using polyester film substrates that are coated with the cyanate acrylate based adhesive product.

Figure 5A:
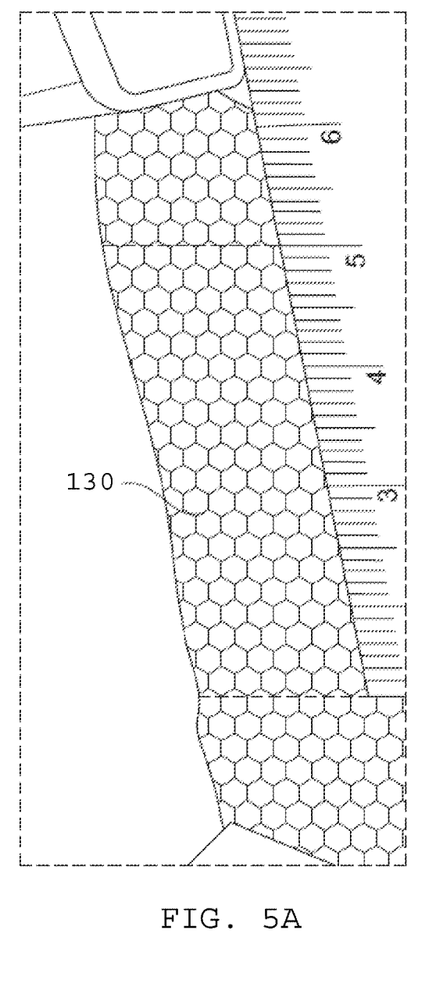
FIG. 5A shows a first stage of a stretch test used to evaluate the performance of a two-part silicone based topical skin adhesive that has been applied to a synthetic mesh, in accordance with one embodiment of the present patent application.
Figure 5B:
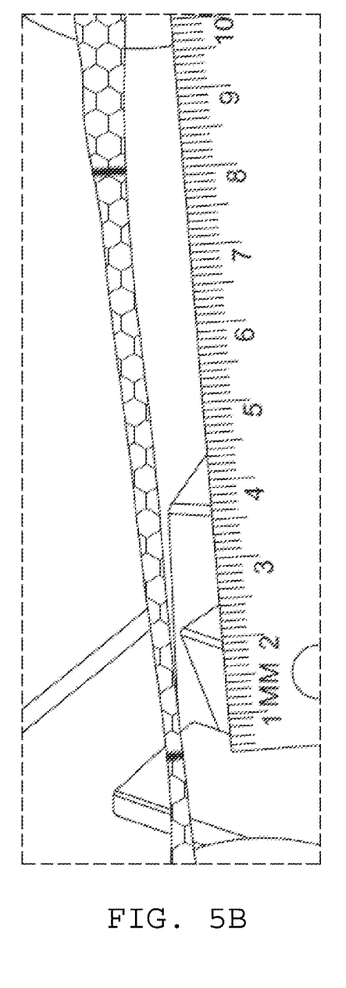
FIG. 5B shows a second stage of a stretch test used to evaluate the performance of a two-part silicone based topical skin adhesive that has been applied to a synthetic mesh, in accordance with one embodiment of the present patent application.
Figure 5C:
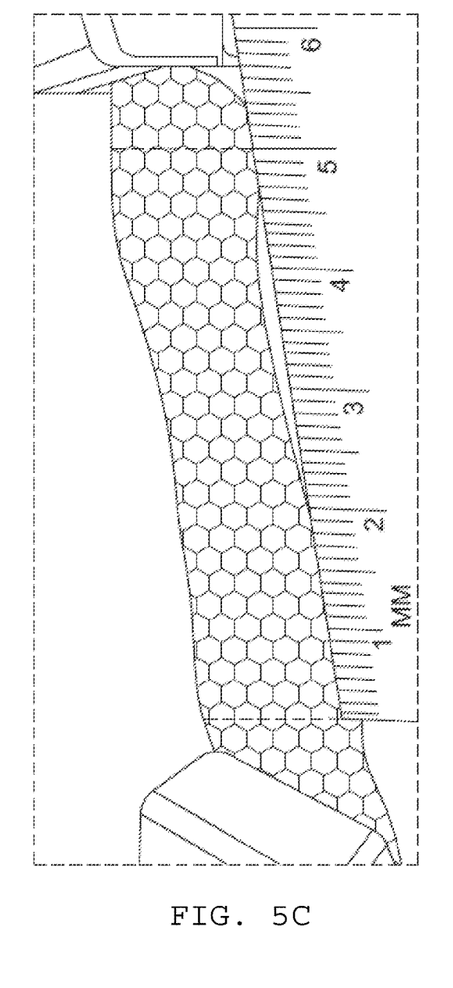
FIG. 5C shows a third stage of a stretch test used to evaluate the performance of a two-part silicone based topical skin adhesive that has been applied to a synthetic mesh, in accordance with one embodiment of the present patent application.

Stretch Test. Referring to FIG. 5A, a test specimen 130 coated with the two-part silicone based topical skin adhesive disclosed for Example 3 above was stretch to 160% of its original length. The dimension of the test specimen 130 was measured before stretching (FIG. 5A) and after stretching (FIG. 5B). Referring to FIG. 5C, after the tension applied to the test specimen 130 was released, the test specimen fully recovered back to its original dimension.

In contrast, a test specimen coated with a cyanate acrylate based topical skin adhesive product was stretched to 101% of its original length. When tension was released, the test specimen did not return to its original dimension. It was observed that a one percent (1%) stretch of the test specimen coated with the cyanate acrylate based topical skin adhesive was all that was required to create a permanent deformation of the polyester film substrate.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. An aerosol spray device comprising:
a container including first and second fluid reservoirs disposed therein that are divided from one another;
said first fluid reservoir holding a first mixture including a first aerosol propellant and a first part of a silicone based topical skin adhesive that is dissolved in said first aerosol propellant;
said second fluid reservoir holding a second mixture including a second aerosol propellant and a second part of said silicone based topical skin adhesive that is dissolved in said second aerosol propellant;
wherein said first part of said silicone based topical skin adhesive comprises a vinyl-terminated polydimethylsiloxane polymer, and wherein said second part of said silicone based topical skin adhesive comprises a vinyl-terminated polydimethylsiloxane polymer;
an aerosol spray dispensing system connected with said container that is configured to combine said first and second mixtures to form said silicone based topical skin adhesive and dispense said silicone based topical skin adhesive from said container as an aerosol spray.

2. The aerosol spray device as claimed in claim 1; wherein said first mixture comprises a catalyst adapted to precipitate a chemical reaction between said first and second parts of said silicone based topical skin adhesive.

3. The aerosol spray device as claimed in claim 2; wherein said catalyst comprises a platinum tetramethyldivinyl disiloxane diethyl maleate complex having the formula:

Pt[(CH$_2$=CH)(CH$_3$)$_2$Si]$_2$O·(COCH=CHCO)(C$_2$H$_5$O)$_2$.

4. The aerosol spray device as claimed in claim 1, further comprising:
said first mixture including first silica particles homogenously dispersed in said first aerosol propellant;
said second mixture including second silica particles homogenously dispersed in said second aerosol propellant.

5. The aerosol spray device as claimed in claim 1, wherein said second mixture further comprises a chain extender mixed with said second part of said silicone based topical skin adhesive.

6. The aerosol spray device as claimed in claim 5, wherein said chain extender comprises silicon hydrid (SiH) terminated polydimethylsiloxane.

7. The aerosol spray device as claimed in claim 1, wherein said first and second aerosol propellants comprise low boiling point hydrocarbon compounds.

8. The aerosol spray device as claimed in claim 7, wherein said low boiling point hydrocarbon compounds are selected from the group consisting of hexane, pentane, butane, isobutene, propane, fluorinated solvents including 1,1-difluoroethane and Solstice® Performance Fluid, ethers including dimethyl ether and diethyl ethyl, and mixtures thereof.

9. The aerosol spray device as claimed in claim 1, wherein said aerosol spray dispensing system comprises:
a dispensing nozzle connected with an upper end of said container for dispensing said aerosol spray of said silicone based topical skin adhesive;
a dip tube disposed inside said container having an upper end in fluid communication with said dispensing nozzle, and a lower end having a first opening in fluid communication with said first fluid reservoir and a second opening in fluid communication with said second fluid reservoir;
a fluid control valve located inside said container between said dip tube and said dispensing nozzle;
a static mixer extending between said dip tube and said valve for combining said first and second mixtures together to form said silicone based topical skin adhesive.

10. An aerosol spray device comprising:
a container including first and second fluid reservoirs disposed therein that are isolated from one another;
said first fluid reservoir holding a first mixture including a first aerosol propellant, a first part of a silicone based topical skin adhesive that is dissolved in said first aerosol propellant, and first silica particles homogeneously dispersed in said first aerosol propellant;
said second fluid reservoir holding a second aerosol propellant, a second part of said silicone based topical skin adhesive that is dissolved in said second aerosol propellant, and second silica particles homogeneously dispersed in said second aerosol propellant;
wherein said first silica particles comprise first silica fume particles homogenously dispersed in said first propellant, and wherein said second silica particles comprise second silica fume particles homogenously dispersed in said second propellant;
an aerosol spray dispensing system connected with said container that is configured to combine said first and second mixtures for forming said silicone based topical skin adhesive and dispensing said silicone based topical skin adhesive from said container as an aerosol spray.

11. The aerosol spray device as claimed in claim 10, wherein said first and second propellants comprise low boiling point hydrocarbon compounds.

12. The aerosol spray device as claimed in claim 11, wherein said low boiling point hydrocarbon compounds are selected from the group consisting of hexane, pentane, butane, isobutene, propane, fluorinated solvents including 1,1-difluoroethane and Solstice® Performance Fluid, ethers including dimethyl ether and diethyl ethyl, and mixtures thereof.

13. The aerosol spray device as claimed in claim 10, wherein said first mixture further comprises a catalyst mixed with said first part of said silicone based topical skin adhesive, wherein said catalyst comprises a platinum tetramethyldivinyl disiloxane diethyl maleate complex having the formula:

Pt[(CH$_2$=CH)(CH$_3$)$_2$Si]$_2$O·(COCH=CHCO)(C$_2$H$_5$O)$_2$

14. The aerosol spray device as claimed in claim 10, wherein each of said first and second parts of said silicone based topical skin adhesive comprises a vinyl-terminated polydimethylsiloxane polymer.

15. The aerosol spray device as claimed in claim 10, wherein said second mixture further comprises a cross-linker and a chain extender mixed with said second part of said silicone based topical skin adhesive.

16. The aerosol spray device as claimed in claim 15, wherein said cross-linker comprises polymethyl hydro siloxane and said chain extender comprises SiH terminated polydimethylsiloxane.

17. The aerosol spray device as claimed in claim 10, wherein said aerosol spray dispensing system comprises:
a dispensing nozzle connected with an upper end of said container;
a dip tube disposed inside said container having an upper end in fluid communication with said dispensing nozzle, and a lower end having a first opening in fluid communication with said first fluid reservoir and a second opening in fluid communication with said second fluid reservoir;
a fluid control valve located inside said container and being located between the upper end of said dip tube and said dispensing nozzle;
a static mixer located between said dip tube and said valve for mixing together the contents of said first mixture of said first fluid reservoir with the contents of said second mixture of said second fluid reservoir.

18. An aerosol spray device comprising:
a container including first and second fluid reservoirs disposed therein that are divided from one another;
said first fluid reservoir containing a first mixture including a first part of a silicone based topical skin adhesive;
said second fluid reservoir containing a second mixture including a second part of said silicone based topical skin adhesive;
an aerosol spray dispensing system connected with said container that is configured to combine said first and second mixtures for forming said silicone based topical skin adhesive and dispensing said silicone based topical skin adhesive from said container as an aerosol spray;
said first part of said silicone based topical skin adhesive including a vinyl-terminated polydimethyl silicone polymer;
said first mixture further comprising silica fume particles, a catalyst, low molecular weight vinyl-terminated polydimethyl silicone polymer, and pentane;
said second part of said silicone based topical skin adhesive including a vinyl-terminated polydimethyl silicone polymer; and
said second mixture further comprising silica fume particles, a polymethyl hydro siloxane cross linker, a SiH terminated polydimethylsiloxane chain extender, and pentane, wherein said catalyst comprises a platinum tetramethyldivinyl disiloxane diethyl maleate complex having the formula:

$$Pt[(CH_2=CH)(CH_3)_2Si]_2O \cdot (COCH=CHCO)(C_2H_5O)_2$$

19. An aerosol spray device comprising:
a container including first and second fluid reservoirs disposed therein that are divided from one another;
said first fluid reservoir containing a first mixture including a first part of a silicone based topical skin adhesive;
said second fluid reservoir containing a second mixture including a second part of said silicone based topical skin adhesive;
an aerosol spray dispensing system connected with said container that is configured to combine said first and second mixtures for forming said silicone based topical skin adhesive and dispensing said silicone based topical skin adhesive from said container as an aerosol spray;
said first part of said silicone based topical skin adhesive including a vinyl-terminated polydimethyl silicone polymer;
said first mixture further comprising silica fume particles, a catalyst, low molecular weight vinyl-terminated polydimethyl silicone polymer, and hexane;
said second part of said silicone based topical skin adhesive including a vinyl-terminated polydimethyl silicone polymer; and
said second mixture further comprising silica fume particles, a polymethyl hydro siloxane cross linker, a SiH terminated polydimethylsiloxane chain extender, and hexane, wherein said catalyst comprises a platinum tetramethyldivinyl disiloxane diethyl maleate complex having the formula:

$$Pt[(CH_2=CH)(CH_3)_2Si]_2O \cdot (COCH=CHCO)(C_2H_5O)_2$$

20. An aerosol spray device comprising:
a container including first and second fluid reservoirs disposed therein that are divided from one another;
said first fluid reservoir containing a first mixture including a first part of a silicone based topical skin adhesive;
said second fluid reservoir containing a second mixture including a second part of said silicone based topical skin adhesive;
an aerosol spray dispensing system connected with said container that is configured to combine said first and second mixtures for forming said silicone based topical skin adhesive and dispensing said silicone based topical skin adhesive from said container as an aerosol spray;
said first part of said silicone based topical skin adhesive including a vinyl-terminated polydimethyl silicone polymer;
said first mixture further comprising silica fume particles, a catalyst, low molecular weight vinyl-terminated polydimethyl silicone polymer, diehtyl ethyl, and pentane;
said second part of said silicone based topical skin adhesive including a vinyl-terminated polydimethyl silicone polymer; and
said second mixture including silica fume particles, a polymethyl hydro siloxane cross linker, a SiH terminated polydimethylsiloxane chain extender, diethyl ether, and pentane, wherein said catalyst comprises a platinum tetramethyldivinyl disiloxane diethyl maleate complex having the formula:

$$Pt[(CH_2=CH)(CH_3)_2Si]_2O \cdot (COCH=CHCO)(C_2H_5O)_2.$$

\* \* \* \* \*